(12) United States Patent
Kumar (10) Patent No.: US 12,357,217 B2
(45) Date of Patent: Jul. 15, 2025

(54) INTEGRATED SPORT ELECTROCARDIOGRAMY SYSTEM (71) Applicant: AliveCor, Inc.

(72) Inventor: David Kumar, San Jose, CA (US)

(73) Assignee: ALIVECOR, INC., Mountain View, CA (US)

(*) Notice: Subject to any disclaimer, the term of this patent is extended or adjusted under 35 U.S.C. 154(b) by 890 days.

(21) Appl. No.: 17/213,063

(22) Filed: Mar. 25, 2021

(65) Prior Publication Data

US 2021/0212625 A1 Jul. 15, 2021

Related U.S. Application Data (60) Continuation-in-part of application No. 16/440,738, filed on Jun. 13, 2019, now Pat. No. 11,103,175, which is a continuation of application No. 15/923,699, filed on Mar. 16, 2018, now Pat. No. 10,342,444, which is a continuation-in-part of application No. 15/721,038, filed on Sep. 29, 2017, now Pat. No. 9,986,925, and a continuation-in-part of application No. 15/486,777, filed on Apr. 13, 2017, now Pat. No. 11,382,554, said application No. 15/721,038 is a continuation of application No. 15/140,072, filed on Apr. 27, 2016, now Pat. No.

(Continued)

(51) Int. Cl.
| | |
|---|---|
| *A61B 5/316* | (2021.01) |
| *A61B 5/00* | (2006.01) |
| *A61B 5/0245* | (2006.01) |
| *A61B 5/25* | (2021.01) |
| *A61B 5/327* | (2021.01) |
| *A61B 5/332* | (2021.01) |
| *A61B 5/333* | (2021.01) |
| *A61B 5/339* | (2021.01) |
| *A61B 5/349* | (2021.01) |
| *G06Q 50/22* | (2018.01) |
| *A61B 5/0205* | (2006.01) |

(52) U.S. Cl.
CPC ............ *A61B 5/316* (2021.01); *A61B 5/0006* (2013.01); *A61B 5/0015* (2013.01); *A61B 5/002* (2013.01); *A61B 5/0022* (2013.01); *A61B 5/0245* (2013.01); *A61B 5/25* (2021.01); *A61B 5/327* (2021.01); *A61B 5/332* (2021.01); *A61B 5/333* (2021.01); *A61B 5/339* (2021.01); *A61B 5/349* (2021.01); *A61B 5/6898* (2013.01); *A61B 5/7225* (2013.01); *G06Q 50/22* (2013.01); *A61B 5/0205* (2013.01); *A61B 5/7257* (2013.01); *A61B 2560/0412* (2013.01)

(58) Field of Classification Search
CPC ................................. A61B 5/316; A61B 5/327
USPC ......................................................... 600/523
See application file for complete search history.

(56) References Cited

U.S. PATENT DOCUMENTS

2014/0031703 A1* 1/2014 Rayner ................ A61B 5/1118
600/484
2019/0350530 A1* 11/2019 Raso ...................... A61B 5/721

* cited by examiner

*Primary Examiner* — Nadia A Mahmood
(74) *Attorney, Agent, or Firm* — WOMBLE BOND DICKINSON (US) LLP (57) ABSTRACT

An apparatus includes sporting equipment, a sensor assembly, and a processing device. The sensor assembly includes a first sensor and a second sensor that are integrated into the sporting equipment to contact skin of a user. The sensor assembly produces electrical signals indicative of physiological signals of the user. The processing device generates an electrocardiogram (ECG) based on the electrical signals.

17 Claims, 7 Drawing Sheets

Related U.S. Application Data

9,833,158, which is a continuation of application No. 14/254,310, filed on Apr. 16, 2014, now Pat. No. 9,351,654, said application No. 15/486,777 is a continuation of application No. 13/964,490, filed on Aug. 12, 2013, now Pat. No. 9,649,042, said application No. 14/254,310 is a continuation-in-part of application No. 13/108,738, filed on May 16, 2011, now abandoned, which is a continuation-in-part of application No. 12/796,188, filed on Jun. 8, 2010, now Pat. No. 8,509,882, said application No. 13/964,490 is a division of application No. 12/796,188, filed on Jun. 8, 2010, now Pat. No. 8,509,882.

(60) Provisional application No. 62/994,621, filed on Mar. 25, 2020.

INTEGRATED SPORT ELECTROCARDIOGRAMY SYSTEM

CROSS-REFERENCE TO RELATED APPLICATION

This application is a continuation-in-part of U.S. patent application Ser. No. 16/440,738, filed Jun. 13, 2019, which is a continuation of U.S. patent application Ser. No. 15/923,699, filed Mar. 16, 2018, now U.S. Pat. No. 10,342,444, which is a continuation-in-part of U.S. patent application Ser. No. 15/721,038, filed Sep. 29, 2017, now U.S. Pat. No. 9,986,925, which is a continuation of U.S. patent application Ser. No. 15/140,072, filed Apr. 27, 2016, now U.S. Pat. No. 9,833,158, which is a continuation of U.S. patent application Ser. No. 14/254,310, filed Apr. 16, 2014, now U.S. Pat. No. 9,351,654, which is a continuation-in-part of U.S. patent application Ser. No. 13/108,738, filed May 16, 2011, now abandoned, which is a continuation-in-part of U.S. patent application Ser. No. 12/796,188, filed Jun. 8, 2010, now U.S. Pat. No. 8,509,882. U.S. patent application Ser. No. 16/440,738 is also a continuation of U.S. patent application Ser. No. 15/923,699, filed Mar. 16, 2018, now U.S. Pat. No. 10,342,444, which is a continuation-in-part of U.S. patent application Ser. No. 15/486,777, filed Apr. 13, 2017, which is a continuation of U.S. patent application Ser. No. 13/964,490, filed Aug. 12, 2013, now U.S. Pat. No. 9,649,042, which is a divisional of U.S. patent application Ser. No. 12/796,188, filed Jun. 8, 2010, now U.S. Pat. No. 8,509,882. This application also claims the benefit of, and priority to, U.S. Provisional Application No. 62/994,621, filed Mar. 25, 2020, and titled "INTEGRATED SPORT ELECTROCARDIOGRA SYSTEM". The disclosure of each of the above applications is herein incorporated by reference in its entirety.

TECHNICAL FIELD

The presently claimed and disclosed inventive concept(s) relates generally to personal physiology monitoring devices and methods and, more particularly, but not by way of limitation, to devices, systems and software for providing ECG, heart rate and cardiac arrhythmia monitoring utilizing a computing device such as a smartphone.

SUMMARY

Embodiments of the presently claimed and disclosed invention are directed to a personal monitoring device having a sensor assembly configured to sense physiological signals upon contact with a user's skin. The sensor assembly produces electrical signals representing the sensed physiological signals. A converter assembly, integrated with, and electrically connected to the sensor assembly, converts the electrical signals generated by the sensor assembly to a frequency modulated physiological audio signal. In one embodiment, the frequency modulated physiological audio signal has a carrier frequency in the range of from about 6 kHz to about 20 kHz.

In another embodiment, the personal monitoring device includes a cable connected to the converter assembly for transmitting the frequency modulated physiological audio signal to a 3.5 mm headphone jack on a smartphone, wherein the converter assembly is electrically isolated from the smartphone by an audio isolation transformer. In this case, the frequency modulated physiological audio signal has a carrier frequency in the range of from about 1 kHz to about 20 kHz.

In yet another embodiment, the personal monitoring device includes a wireless radio transmitter configured to utilize Bluetooth® headset technology to transmit the frequency modulated physiological audio signal, having a carrier frequency in the range of from about 1 kHz to about 20 kHz, to a Bluetooth® enabled computing device.

An ECG device of the presently claimed and disclosed inventive concept(s) includes an electrode assembly configured to sense heart-related signals upon contact with a user's skin, and to convert the sensed heart-related signals to an ECG electric signal. A converter assembly, integrated with, and electrically connected to the electrode assembly, is configured to convert the electric ECG signal generated by electrode assembly to a frequency modulated ECG audio signal having a carrier frequency in the range of from about 6 kHz to about 20 kHz.

In one embodiment, a smartphone protective case, usable as an ECG device, is provided. An electrode assembly, configured to sense heart-related signals upon contact with a user's skin, and to convert the sensed heart-related signals to an ECG electric signal, is provided. A converter assembly, integrated with, and electrically connected to the electrode assembly, is configured to convert the electric ECG signal generated by the electrode assembly to a frequency modulated ECG audio signal having a carrier frequency in the range of from about 6 kHz to about 20 kHz, and further configured to output the ECG audio signal through an audio transmitter at a signal strength capable of being received by a smartphone positioned within the smartphone protective case.

In a second embodiment, an ECG device is provided in a housing having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal having a carrier frequency in the range of from about 6 kHz to about 20 kHz, and further configured to output the ECG audio signal through an audio transmitter at a signal strength capable of being received by a smartphone located near the ECG device.

In another embodiment, an ECG device is provided having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal. A cable is provided for transmitting the frequency modulated ECG audio signal to a 3.5 mm headphone jack on a smartphone, wherein the converter assembly is electrically isolated from the smartphone by an audio isolation transformer.

In yet another embodiment, a computer-readable storage medium is provided for storing a set of instructions capable of being executed by one or more computing devices, causing the one or more computing devices to digitize and demodulate a frequency modulated ECG audio signal having a carrier frequency in the range of from about 6 kHz to about 20 kHz to produce real time demodulated digital ECG data, and to display on a display screen of the computing device, the real time ECG signal represented by the demodulated digital ECG data.

In yet another embodiment, an apparatus includes sporting equipment, a sensor assembly, and a processing device. The sensor assembly includes a first sensor and a second sensor that are integrated into the sporting equipment to contact skin of a user. The sensor assembly produces electrical signals indicative of physiological signals of the user. The processing device generates an electrocardiogram (ECG) based on the electrical signals.

In yet another embodiment, a system includes sporting equipment, a processing device, and a mobile device. The sporting equipment includes a body and a sensor assembly. The sensor assembly includes a first sensor and a second sensor that are integrated into the body to contact skin of a user. The sensor assembly produces electrical signals indicative of physiological signals of the user. The processing device operatively coupled to the sensor assembly to d generate electrocardiogram (ECG) data based on the electrical signals. The mobile device displays the ECG data. The mobile device communicatively coupled to the sporting equipment to display the ECG data.

In yet another embodiment, a method includes recording a first electrocardiogram (ECG) of a user, recording a second ECG of the user, analyzing the first ECG and the second ECG, and providing an indication corresponding to a health metric of the user based on the analyzing. Recording the first ECG and the second ECG includes the user contacting an electrode assembly of an ECG device integrated into the sporting equipment. Recording the first ECG occurs before activity has begun and recording the second ECG occurs after the activity has finished.

Thus, utilizing (1) the technology known in the art; (2) the above-referenced general description of the presently claimed and disclosed inventive concept(s); and (3) the detailed description of the invention that follows, the advantages and novelties of the presently claimed and disclosed inventive concept(s) would be readily apparent to one of ordinary skill in the art.

DETAILED DESCRIPTION

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

Figure 1:
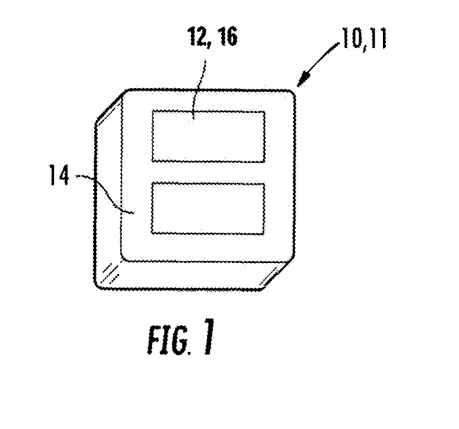
FIG. 1 is a schematic representation of an embodiment of a personal monitoring device of the present disclosure.
Figure 2:
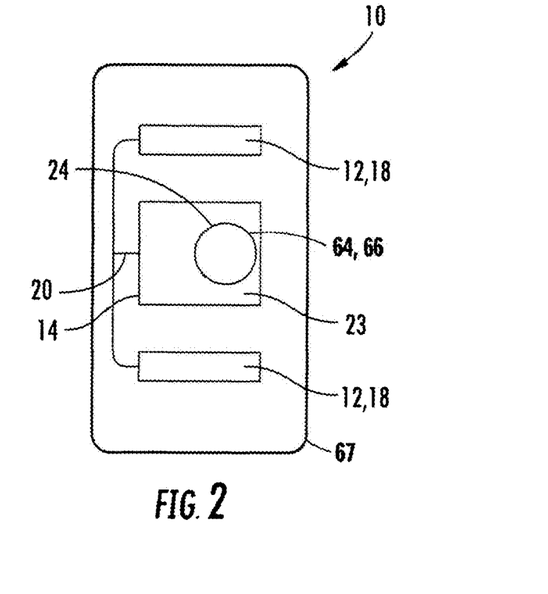
FIG. 2 is a schematic representation of another embodiment of a personal monitoring device of the present disclosure.

The presently claimed and disclosed inventive concepts provide a personal monitoring device 10, embodiments of which are shown schematically in FIGS. 1 and 2. The acquisition electronics 11 of the monitoring device 10 includes a sensor assembly 12 configured to sense physiological signals upon contact with a user's skin. The sensor assembly 12 produces electrical signals representing the sensed physiological signals, which input to a converter assembly 14, integrated with the sensor assembly 12. Converter assembly 14 converts the electrical signals generated by the sensor assembly 12 to a frequency modulated physiological audio signal having a carrier frequency in the range of from about 1 kHz to about 20 kHz. In one embodiment, the frequency modulated physiological audio signal has a carrier frequency in the range of from about 6 kHz to about 20 kHz.

The sensor assembly 12 can include any suitable sensor operative to detect a physiological signal that a user desires to monitor. Nonlimiting examples of such physiological signals include, but are not limited to, respiration, heartbeat, heart rate, electrocardiogram (ECG), electromyogram (EMG), electrooculogram (EOG), pulse oximetry, photoplethysmogram (PPG) and electroencephalogram (EEG).

Figure 3:
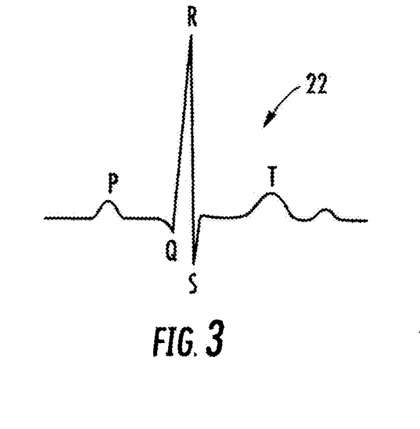
FIG. 3 is an example of graphical ECG representation.

A respiration detector can be a conventional microphone assisted stethoscope 16. Heart beat and heart rate can be detected as well using a conventional microphone assisted stethoscope 16, or by using an electrode assembly 18 to sense electrical signals generated by the heart over time. Such electrodes 18 can also be used to detect the electrical activity of the heart over time for electrocardiograman ECG is a measurement of the small electrical changes on the skin generated when the heart muscle depolarizes during each heart beat. The output from a pair of electrodes 18 is known as a lead 20. Small rises and falls in the voltage between two electrodes placed on either side of the heart can be processed to produce a graphical ECG representation 22 such as the example ECG shown in FIG. 3.

Electromyography (EMG) detects the electrical potential generated by muscle cells when the cells are electrically or neurologically activated. The signals can be analyzed to detect medical abnormalities. Electrooculography (EOG) is a technique for measuring the resting potential of the retina. Usually, pairs of electrodes 18 are placed either above and below the eye, or to the left and right of the eye, and a potential difference measurement is a measure for the eye position.

The oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. An electroencephelogram (EEG) can be monitored using electrodes attached to the scalp and measures voltages generated by brain activity.

The converter assembly 14 converts the electrical signals generated by the sensor assembly 12 to a frequency modulated physiological audio signal that can be received by a computing device 13. In the embodiment shown in FIG. 2, the converter assembly 14 includes a converter 23 and an audio transmitter 24 for outputting frequency modulated physiological signals having a carrier frequency in the range of from about 6 kHz to about 20 kHz as frequency modulated acoustic signals. Nonlimiting examples of suitable audio transmitters 24 include, but are not limited to, miniature speakers, piezoelectric buzzers, and the like. The acoustic signals can be received by, for example, a microphone 25 in a computing device 13 such as a smartphone, personal digital assistant (PDA), tablet personal computer, pocket personal computer, notebook computer, desktop computer, server computer, and the like.

Prior art devices have used frequency modulated physiological signals to communicate between acquisition hardware and a computing device. The signals have a carrier frequency within the audible range such as the traditional 1.9 kHz FM frequency used to transmit ECG signals. However, it has been discovered that by using "high frequency" audio frequencies as the carrier, such as frequencies in the range of from about 6 kHz to about 20 kHz, the acoustic communication between the acquisition electronics 11 of the personal monitoring device 10, and a computing device 13 such as a smartphone, is virtually silent and far more noise-immune than the traditional 1.9 kHz FM ECG frequency. In fact, measurements of the audio signal power in the 1.5 kHz to 15 kHz range determined that carrier frequencies of 6 kHz and higher provide communication that is immune to ambient and voice "noise" contamination. Also, by using a carrier frequency in the 10 kHz to 15 kHz range, we create both a lower noise and a silent communication between the acquisition electronics 11 and the computing device 13 or smartphone. An additional reason for using high carrier frequencies, such as in the 6 kHz to 15 kHz range or in the 10 kHz to 15 kHz range, is to allow simultaneous recording of voice and physiological signals over a single audio channel, where voice and the FM signal are in different frequency bands that can be filtered and separated. The clinical applications of this embodiment can include fast and inexpensive cardiac rhythm diagnosis for physicians as well as personal ECG acquisition for patients.

Figure 4:
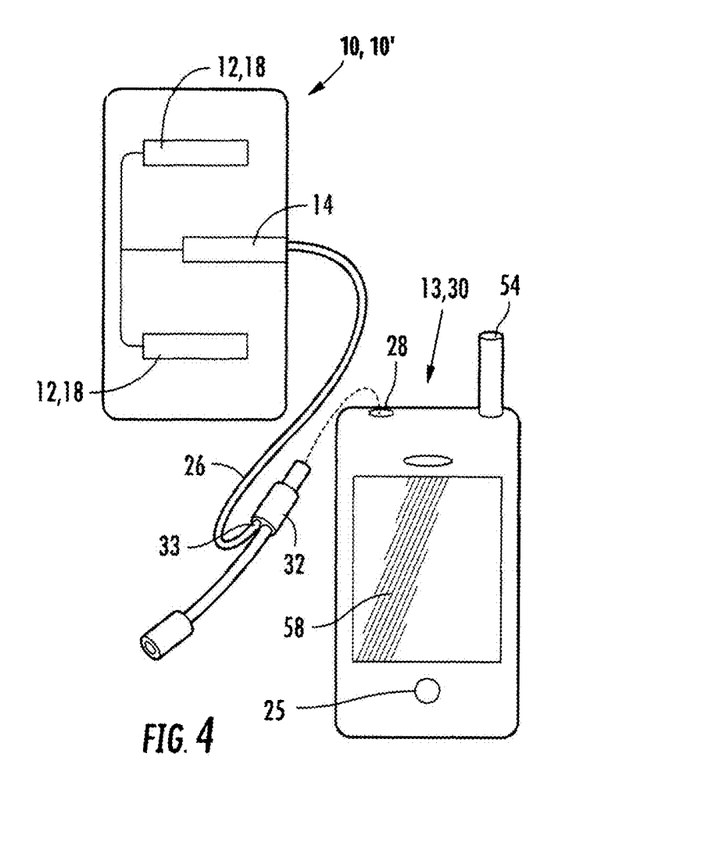
FIG. 4 is a schematic representation of an embodiment wherein a personal monitoring device includes an audio cable that can input to a smartphone.

In another embodiment, such as that shown in FIG. 4, the converter assembly 14 is configured to convert the electrical signals generated by the sensor assembly 12 to a frequency modulated physiological audio signal which is transmitted by a cable 26 to a 3.5 mm headphone jack 28 on a smartphone 30. This configuration is totally silent and immune to ambient acoustic noise. In this embodiment the converter assembly 14 is electrically isolated from the smartphone 30 by an audio isolation transformer 32. The audio isolation transformer 32 preferably conforms to medical safety performance standards such as, for example, those outlined in IEC 60601 along with national and regional deviations. The cable 26 for transmitting the frequency modulated ECG audio signal to the 3.5 mm headphone jack 28 on the smartphone 30 can include a splitter 33 configured, as understood by those skilled in the art, to allow the user to listen to music and voice messages while transmitting the frequency modulated ECG audio signal. The splitter 33 can also allow the user to utilize a mic or headset to record spoken voice messages, such as comments and notes regarding physical symptoms, simultaneously with the ECG audio signal. Using a high carrier frequency of around 10 kHz, or in the 6 kHz to 20 kHz range, allows simultaneous recording of voice and physiological signals over a single audio channel, where the voice and the frequency modulated signal are in different frequency bands that can be readily filtered and separated.

Figure 5:
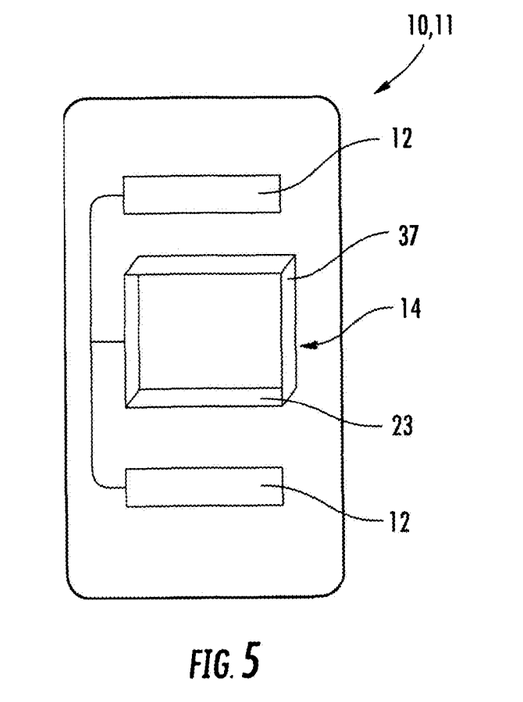
FIG. 5 is a schematic representation of an embodiment of an ECG device of the present invention utilizing a wireless radio transmitter.
Figure 6:
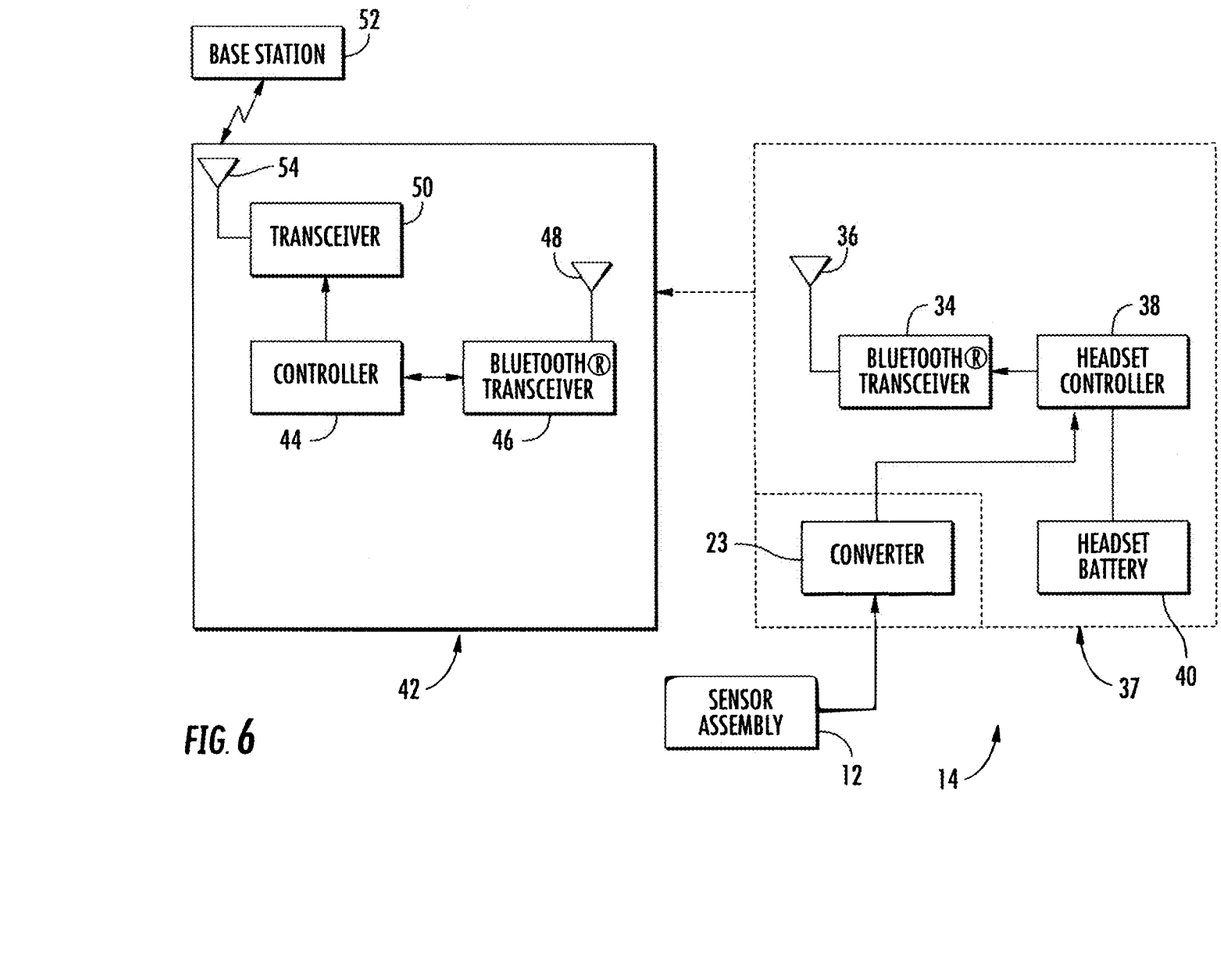
FIG. 6 is a schematic representation of an embodiment of a personal monitoring device of the present disclosure connecting via Bluetooth® to a computing device.

In yet another embodiment, shown in FIGS. 5 and 6, the converter assembly 14 includes a wireless radio transmitter 37 configured to convert and transmit the electrical signals generated by the sensor assembly 12 using a headset profile (HSP) of the Bluetooth® wireless communications standard is defined by the Bluetooth Special Interest Group (SIG) and available at URL address www.bluetooth.org. The electrical signals generated by the sensor assembly 12 are converted and transmitted using a Bluetooth® transceiver 34 and antenna 36 and communicated to the computing device 13, preferably a smartphone 30, according to instructions provided by a headset controller 38. Economy, as well as isolation and convenience, are provided by using a commercially available headset controller 38, Bluetooth® transceiver 34, and antenna 36, powered by a headset 40, wherein the electronics are commercially configured and mass-produced for communicating with computing devices 13 such as smartphones 30.

Computing device electronics 42 typically include a controller 44, a Bluetooth® transceiver 46 and antenna 48 for receiving input from a wireless Bluetooth® device. Most computing devices, and all smartphones, include a memory 56, a display screen 58, and a transceiver 50 for transmitting/receiving information signals to/from a base station or web server 52 via a cellular antenna 54. Thus, the computing device electronics 42 can be used to store information from the personal monitoring device 10 in memory 56, and/or transmit the information to the base station 52 or a specific communication address via wireless communication technology well understood by those skilled in the art.

In some cases, the personal monitoring device 10 can be considered an ECG device 10' and includes an electrode assembly 18 configured to sense heart-related signals upon contact with a user's skin, and to convert the sensed heart-related signals to an ECG electric signal. As discussed in detail hereinafter, the ECG device 10' transmits a frequency modulated ECG audio signal to a smartphone 30 via a wired audio jack connection, a wireless headset, or acoustically. Software running on the smartphone 30 digitizes and processes the audio in real-time, where the frequency modulated ECG signal is demodulated. The ECG can be further processed using algorithms to calculate heart rate and identify arrhythmias. In addition to the display and local processing of the ECG data, the smartphone 30 can transmit, in real-time, the ECG, heart rate and rhythm data via a secure web connection for viewing, storage and further analysis via a web browser interface (using the 2G/3G or WiFi connectivity of the smartphone 30). Server software provides for storage, further processing, real-time or retrospective display and formulation of a PDF ECG rhythm strip document and/or other reports and formats for printing remotely or locally.

In one embodiment, the converter assembly 14 of ECG device 10' is integrated with, and electrically connected to the electrode assembly 18 and is configured to convert the electric ECG signal generated by electrode assembly 18 to a frequency modulated ECG audio signal having a carrier frequency in the range of from about 6 kHz to about 20 kHz. It is sometimes desirable to utilize a carrier frequency in the 10 kHz to 15 kHz range in order to create both a lower noise and a silent communication between the acquisition electronics 11 and the computing device 13 or smartphone 30.

Figure 7:
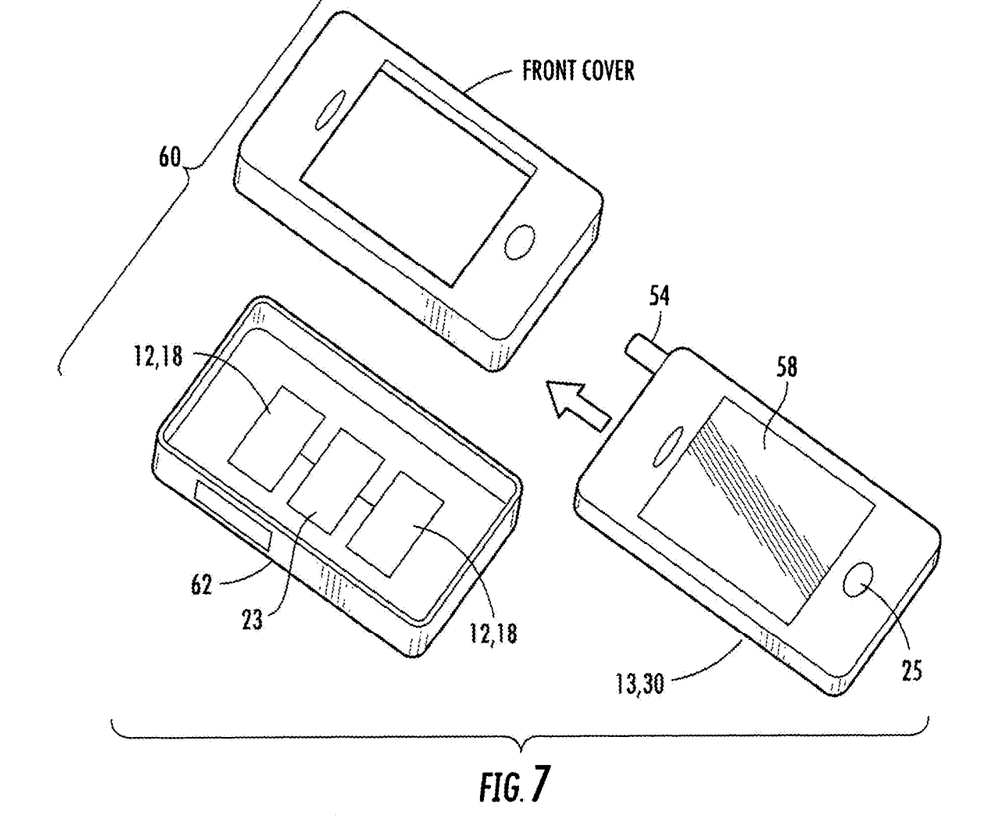
FIG. 7 is a schematic representation of an embodiment of a personal monitoring device of the present disclosure.

In one configuration, the ECG device 10' is usable as a smartphone protective case 60 as shown in FIG. 7. One example configuration utilizes a "slip-on" protective case 60 for an iPhone® or other smartphone 30, the protective case 60 including an integrated ECG electrode assembly 18 and acquisition electronics 11 (2, 3 or 4 electrodes for generating a single lead of ECG data). The ECG electrodes are located on the side 62 of the case 60 opposite of the display screen 58. The smartphone 30, in its ECG-adapted protective case 60, is held in both hands (generating a lead one, Left Arm minus Right Arm) or is placed on a person's chest to generate a modified chest lead. The ECG is measured by the acquisition electronics 11 and converted into a frequency modulated signal with a carrier or center frequency from about 6 kHz to 20 kHz, or in some embodiments from 10 kHz to 15 kHz. The frequency modulated signal is output by a miniature speaker 64 or a piezoelectric buzzer 66 (FIG. 2).

In another configuration, the ECG device 10', as shown schematically in FIG. 2, is usable as a standalone real-time ECG acquisition device. The ECG device is identical to the "case" electronics, but is present in its own housing 67 rather than being integrated into a protective case 60 for a smartphone 30. This embodiment allows for use of the device to acquire ECG data and have it communicated acoustically to a PC or other computing device for demodulation, processing, storage and display via a web application and connection.

In either configuration, the smartphone 30 utilizes its built-in microphone 25 and CPU to acquire, digitize, demodulate, process and then display the ECG data in real-time. Also, the smartphone 30 can calculate a real-time heart rate measurement and determine a cardiac rhythm diagnosis like atrial fibrillation. The smartphone 30 can utilize its 2G, 3G, Bluetooth® and WiFi connectivity to transmit the ECG and other data to a secure web server 52 for real-time distant display, storage and analysis. Also, the ECG data can be stored locally on the smartphone 30 for later review or transmission.

Figure 8:
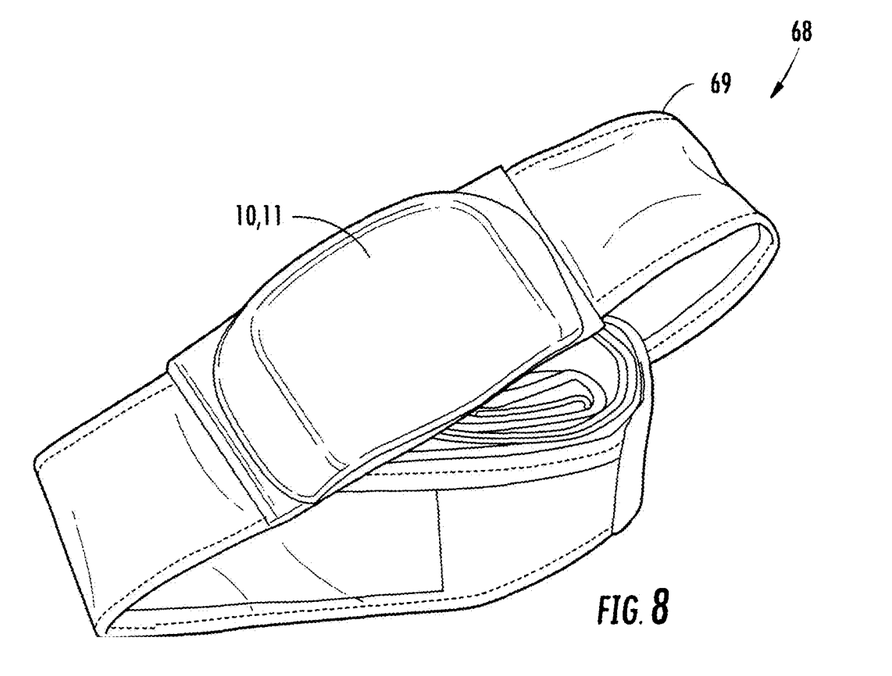
FIG. 8 is a schematic representation of an embodiment of an ECG device of the present invention included positioned within a chest strap.

In another embodiment, shown schematically in FIG. 8, the ECG device 10' is usable as a chest strap device 68 like a fitness heart rate monitor. The chest strap 69 with integrated ECG electrode assembly 18 and acquisition electronics 11 "pod" generate the frequency modulated ECG signal and send it by one of two modes to the smartphone 30. In one mode, a cable 26, as described above, plugs into the 3.5 mm headphone jack 28 on the iPhone®, Blackberry® or other smartphone 30 which provides an audio input (normally used for a headphone mic). This configuration is totally silent and immune to ambient acoustic noise. The ECG data is isolated from the smartphone 30 by an audio isolation transformer 32. In another mode, the frequency modulated audio signal is transmitted by a Bluetooth® headset chip, as described above, and the smartphone 30 receives it and performs the other processing steps. This configuration preferably makes use of mass-produced headset electronics and includes a rechargeable battery. This configuration is wireless, which provides isolation and convenience.

Software on the smartphone 30 can also combine data and signals from other sensors built into the smartphone 30 such as a GPS and accelerometer. Further processing of this data provides additional information related to the user, such as speed, location, distance, steps, cadence, body position, fall detection and energy expenditure. The raw signals from the sensors and derived information can be displayed and stored locally on the smartphone 30, as well as being transmitted to the web server 52 over an Internet connection. Software on the web server 52 provides a web browser interface for real-time or retrospective display of the signals and information received from the smartphone 30, and also includes further analysis and reporting.

Figure 9:
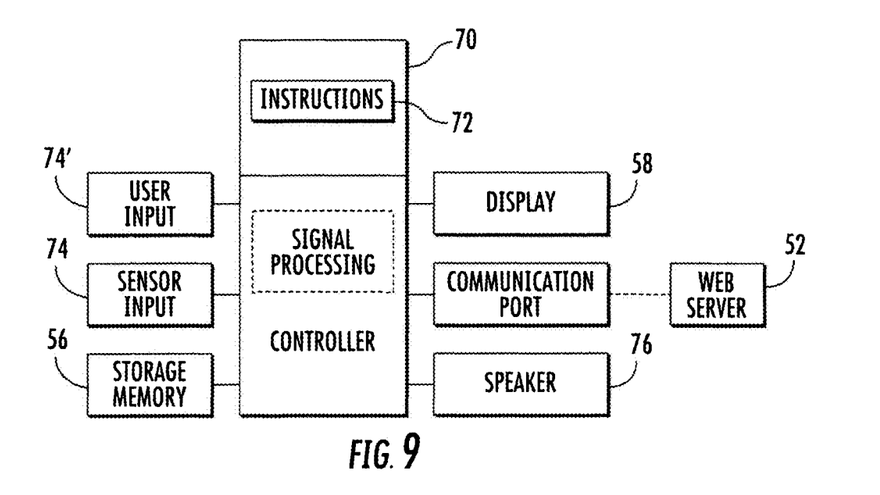
FIG. 9 is a schematic representation of a computer-readable storage medium in accordance with an embodiment of the present disclosure.

Referring now to FIG. 9, a computer-readable storage medium 56 stores a set of instructions 72, wherein the instructions 72 are capable of being executed by one or more computing devices 13. Nonlimiting examples of suitable computing devices 13 include smartphones 30, personal digital assistants (PDAs), tablet personal computers, pocket personal computers, notebook computers, desktop computers, and server computers. When executed, the one or more computing devices 13 is caused to digitize and demodulate a sensor input 74 such as a frequency modulated ECG audio signal having a carrier frequency in the range of from about 6 kHz to about 20 kHz to produce real-time demodulated digital ECG data. The instructions 72 can cause the real-time demodulated digital ECG data to display on a display screen 58 of the computing device 13. The instructions 72 can cause the real-time display of an ECG waveform (FIG. 3) to display on a display screen 58 of the computing device 13. The ECG waveform may represent a Lead I ECG.

Sensor input 74 can also include real-time information from additional sensors as well as user input 74'. For example, in embodiments wherein the computing device 13 is a smartphone 30, the input 74 can include real-time information from a GPS and/or accelerometer in the smartphone 30 in addition to the demodulated digital ECG data. User input 74' can also include spoken voice messages entered through a microphone of the computing device 13. Instructions 72 can cause the sensor and/or user input 74 and 74' to be recorded and maintained in a storage memory 56 of the computing device 13.

In one embodiment, the set of instructions 72, when executed by the one or more computing devices 13, can further cause the one or more computing devices 13 to calculate and display in real-time, a heart rate represented by the frequency modulated ECG audio signal. In addition, demodulated digital ECG data can be processed to identify the occurrence of an arrhythmia. In such designs, the storage medium 70 can include instructions 72 to cause the computing device 13 to display a warning on a display screen 58 or emit an audible alert through the speaker 76 at the occurrence of an arrhythmia.

Instructions 72 can cause the computing device 13 to store the demodulated digital ECG data in a memory 56 of the one or more computing devices 13 for later retrieval. The set of instructions 72 can further cause the one or more computing devices 13 to retrieve and transmit, upon demand, the stored demodulated digital ECG data to a web server 52 via an internet connection on the computing device 13. Recorded spoken voice messages can be stored and transmitted to the web server 52, simultaneously with the demodulated digital ECG data.

In other embodiments, the instructions 72 can cause the one or more computing devices 13 to transmit the demodulated digital ECG data, and/or voice messages, to the web server 52 in real-time.

A version of the smartphone software is packaged as a software library that can be integrated with other third party software applications. This provides a simplified and standard method for third party applications to use the ECG device 10' to obtain heart rate and other derived information without having to develop their own data acquisition, demodulation, and signal processing algorithms.

A version of the software also runs on a PC and includes demodulation, processing, storage and transmission to the web server 52. The software includes the audio acquisition, demodulation, ECG analysis, and acceleration analysis modules.

The audio acquisition module selects the appropriate audio input and samples the audio. On the iPhone®, audio is sampled and processed using the audio unit framework, which provides low latency audio acquisition and processing. The audio unit framework also allows automatic selection of the appropriate audio source, internal mic, audio jack connection, or Bluetooth® headset. The sampling rate will typically be at 44 kHz when the modulation carrier frequency is greater than 10 kHz, but for lower carrier frequencies, it may use a lower audio sampling rate. On other devices this module will use the most appropriate APIs for efficient, low latency audio sampling.

The demodulation module demodulates a frequency modulated ECG audio signal, using a linear approximation and zero crossings algorithm. The demodulator allows selection of different modulation parameters to match the particular ECG device. Demodulation using zero crossings and linear approximation works well for carrier frequencies 6 kHz and lower and has the advantage that it is simple and fast. Above 10 kHz with 44 kHz sampling, the errors from linear approximation become large, although the effect is somewhat reduced if applying a 40 Hz filter to the demodulated ECG. Application of sine or other curve fitting methods can be used to reduce the error associated with linear approximation for carrier frequencies above 10 kHz. Audio samples from the audio acquisition module are first passed through a digital band-pass filter to remove unwanted frequencies outside the modulation range. The digital band-pass filter is most effective when receiving acoustically coupled audio which can be contaminated with noise. When using a center frequency above 6 kHz, the band-pass filter is able to provide good noise immunity from voice and background ambient noise which is typically below 5 kHz. The band-pass filter stage could be eliminated to save processing power when receiving audio via a wired or Bluetooth® connection which would not be susceptible to background noise contamination. To demodulate the signal, it may be necessary to estimate the frequency of the audio waveform. The algorithm looks at the sign of incoming data. When the sign changes it draws a straight line between the two points and interpolates the zero value. It uses this to determine the average frequency over a 3.333 ms interval, which provides ECG data at the output sampling rate of 300 Hz.

The ECG analysis module includes algorithms that process the ECG to detect and classify beats, and provides a heart rate estimate. Beat-to-beat heart rate is calculated from the interval between beats and a more robust measurement of heart rate is calculated using median filtering of the RR intervals.

The acceleration analysis module includes algorithms that process signals from the built-in 3 axis accelerometer sensor in the smartphone 30, to derive an estimate of a person's energy expenditure, steps, cadence, and body position and to detect falls.

Figure 10:
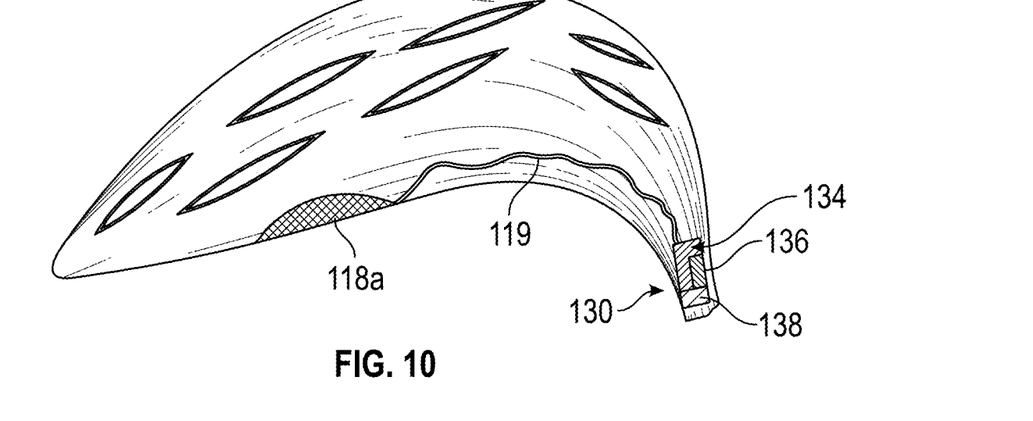
FIG. 10 is a side, schematic representation of a first integrated sport in accordance with an embodiment of the present disclosure.
Figure 11:
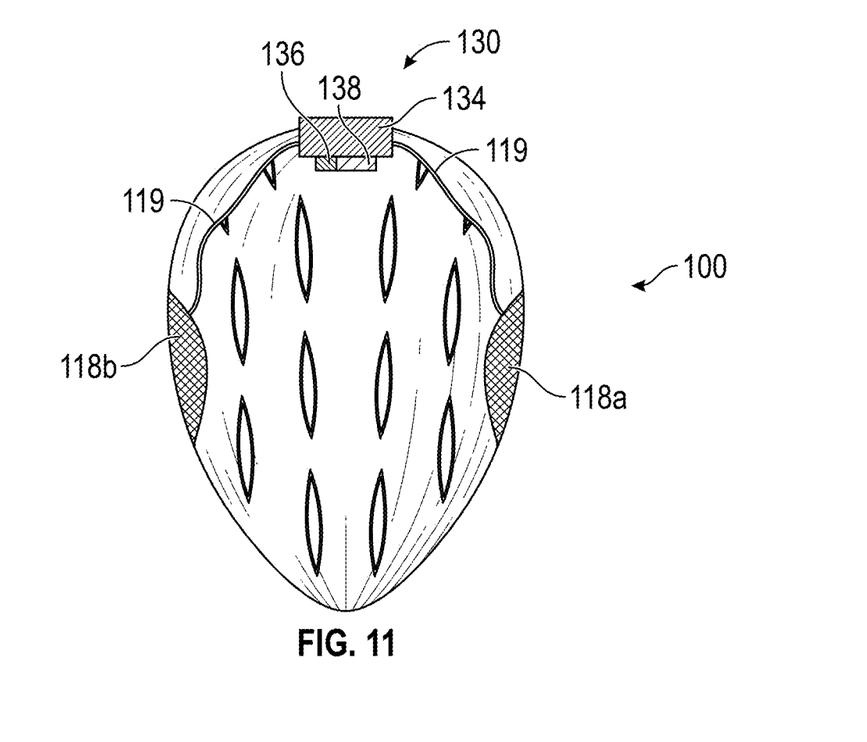
FIG. 11 is a top, schematic representation of the first integrated sport embodiment of FIG. 10.
Figure 12:
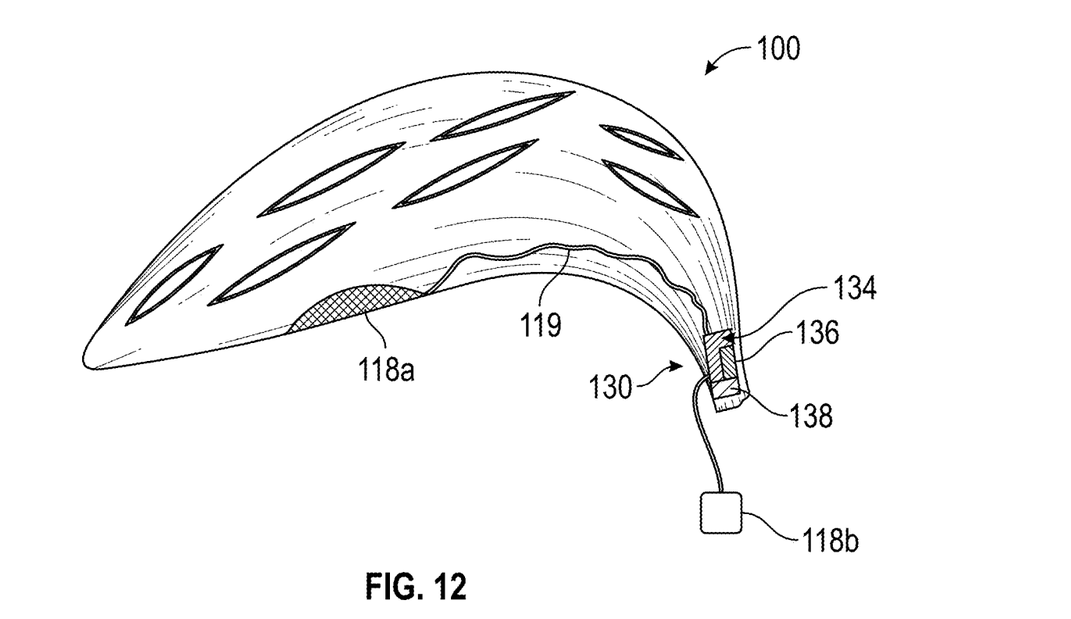
FIG. 12 is a side, schematic representation of a second integrated sport in accordance with an embodiment of the present disclosure

FIGS. 10 and 11 are a schematic representation of a first integrated sport embodiment of the present invention. Referring to FIGS. 10 and 11, as shown, the embodiments described herein may be integrated into a variety of sporting equipment. For example, in one embodiment, the ECG sensors may be integrated into a body of a helmet (e.g., bike, skateboard, motorcycle, scooter, etc.), such as a bike helmet 100 as shown. In one embodiment, left and right electrodes 118a, 118b may be constructed into, or added to, the left and right sides of a helmet such that each electrode 118a, 118b is configured to contact the scalp of a user when the helmet is worn. In some embodiments, the first electrode 118a may be configured to contact the scalp of the user and the second electrode 118b may be configured to contact a limb of the user (e.g., an arm or a leg of a user) as shown in FIG. 12. To contact a limb of the user, the second electrode 118b may be connect to the helmet via a cable or may connect to the helmet via a wireless connection. In certain embodiments, the second electrode 118b may connect to the computing device 13 wirelessly. In other embodiments, more or less than two electrodes may be used. In one embodiment, electrodes may be placed in any suitable area of the helmet, such that the electrodes are able to make contact with the skin of the user (e.g., the scalp of a user). For example, an electrode may be positioned on a front of a helmet in contact with a forehead or brow of a wearer.

In one embodiment, a communications module 130, such as a Printed Circuit Board Assembly (PCBA) Bluetooth module 134 as shown, and a power module 136 (e.g., a battery) may be built into or added to the helmet 100. Such a module 130 may allow for communication with a mobile device, as described herein. Wiring 119 may connect the various sensors and modules (e.g., electrode 118a, 118b or modules 134, 136). In another embodiment, the components are wirelessly connected. In one embodiment, the helmet 100 may contain a processing device 138 to generate an ECG. The processing device 138 may provide an ECG waveform for display on a mobile device. The ECG waveform may represent a Lead I ECG. The processing device 138 may generate and transmit ECG data to a mobile device. In another embodiment, the helmet 100 may include a memory device 156, so that data recorded by the communications module 130 can be stored in the memory 156 before transmitting such data to a mobile device. In one embodiment, the helmet 100 described by FIGS. 10 and 11 allows for the ECG functionality described herein in a helmet form-factor.

Figure 13:
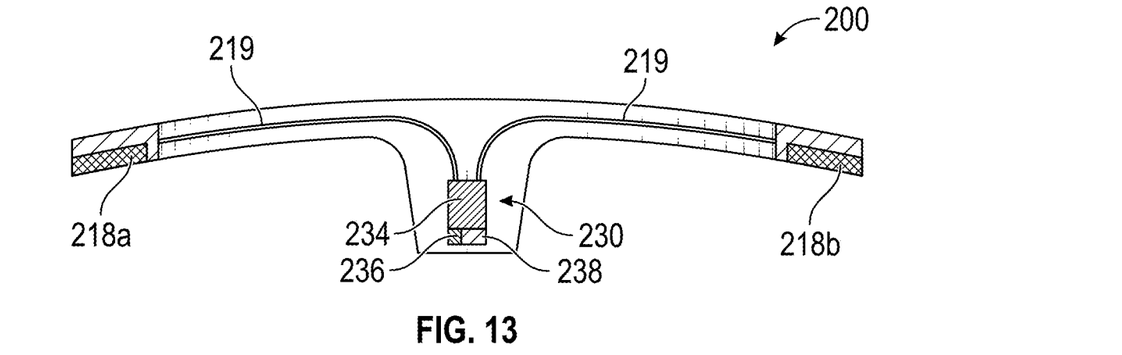
FIG. 13 is a schematic representation of a third integrated sport in accordance with an embodiment of the present disclosure.

FIG. 13 is a schematic representation of another integrated sport embodiment of the present invention. Referring to FIG. 13, as shown, the embodiments described herein may be integrated into a body of a variety of sporting equipment. For example, in one embodiment, the ECG sensors may be integrated into a body of handlebars (e.g., of a bike, motorcycle, scooter, exercise equipment, etc.), such as bike handlebars 200 as shown. In one embodiment, left and right electrodes 218a, 218b may be constructed into, or added to, the left and right sides of such handlebars. In other embodiments, more or less than two electrodes may be used. In one embodiment, electrodes may be placed in any suitable area of the handlebars, such that the electrodes are able to make contact with the skin (e.g., on the hands) of the user.

In one embodiment, a communications module 230, such as a PCBA Bluetooth module 234 as shown, and a power module 236 (e.g., a battery) may be built into or added to the handlebars 200. Such module 230 may allow for communication with a mobile device, as described herein. Wiring 219 may connect the various sensors and modules (e.g., electrode 218a, 218b or modules 234, 236). In another embodiment, the components are wirelessly connected. In one embodiment, the handlebars 200 may contain a processing device 238. The processing device 238 may provide an ECG waveform for display on a mobile device. The ECG waveform may represent a Lead I ECG. The processing device 238 may generate and transmit ECG data to a mobile device. In another embodiment, the handlebars 200 may include a memory device 256, so that data recorded by the communications module 230 can be stored in the memory 256 before transmitting such data to a mobile device. In one embodiment, the handlebars 200 described by FIG. 13 allows for the ECG functionality described herein in a handlebar form-factor.

When integrated into sporting equipment (e.g., helmet 100 or handlebars 200) an ECG device as described herein may detect heart-related signals and other physiological signals generated by a wearer. The other physiological signals may include signals to contract muscles during movement including exercise. For example, the other physiological signals may include signals to contract biceps of the wearer. The other physiological signals may create noise for detecting the heart-related signals.

Figure 14:
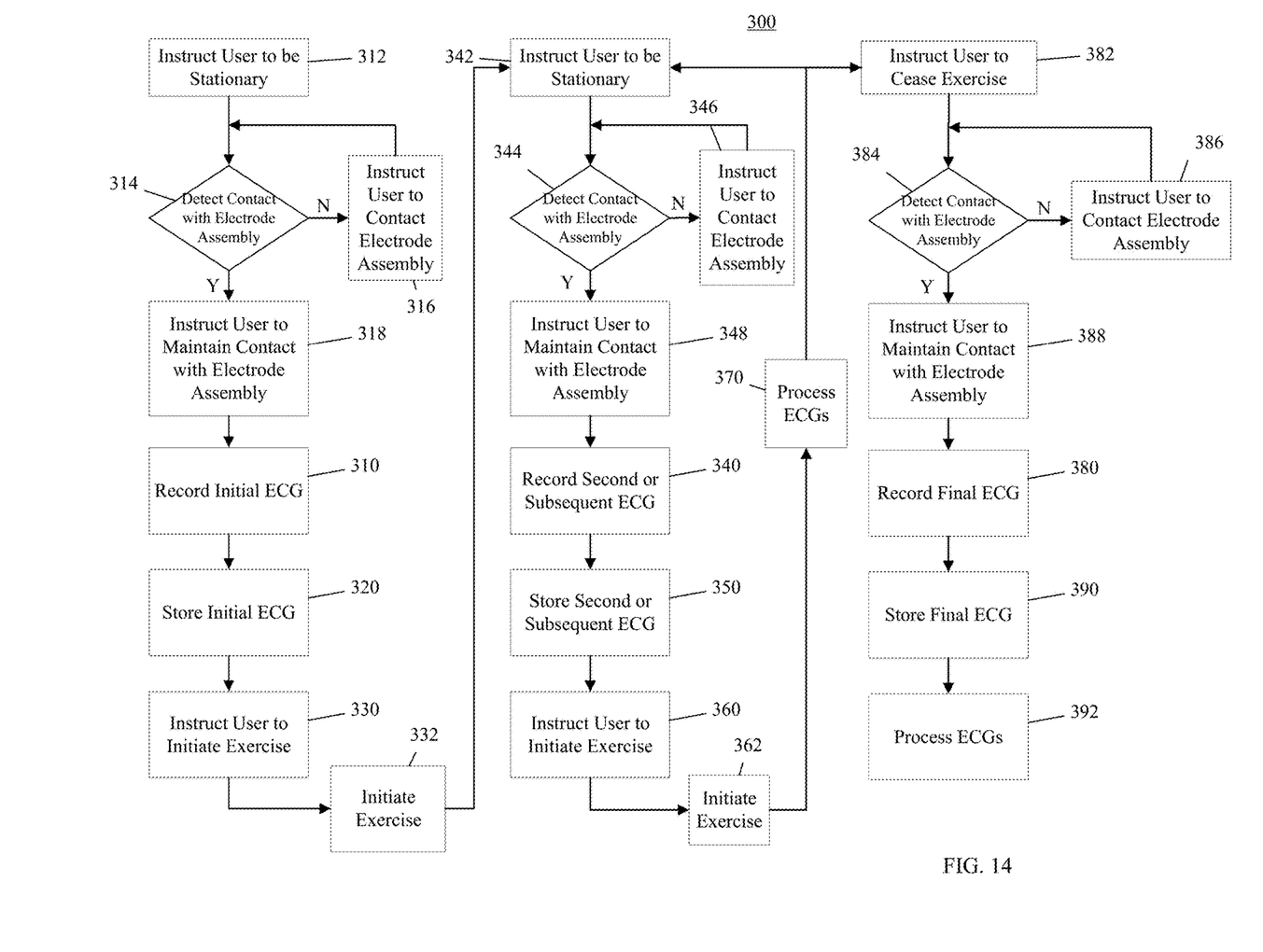
FIG. 14 is a flow chart of a method of taking and processing ECG data in accordance with an embodiment of the present disclosure.

FIG. 14 illustrates a method 300 of detecting and analyzing heart-related signals with an ECG device as described herein. The ECG device may be integrated into sporting equipment including, but not limited to, a helmet 100, handlebars 200, or fitness equipment including handles or handlebars (e.g., a stationary exercise bike, a treadmill, an elliptical machine, or a stair machine). The method 300 may be embodied in non-transitory computer-readable storage medium that is executed on a computing device. For example, the method 300 may be an application executed on a smartphone. The method 300 may include providing instructions to a user to execute one or more steps of the method.

The method 300 includes taking or recording an initial ECG of a user (Step 310). The initial ECG may be taken when the user is stationary or at rest. Before taking the initial ECG, the method 300 may include providing or displaying instructions to the user to be stationary (Step 312). In some embodiments, the ECG device may be integrated into fitness equipment. In such embodiments, the ECG device may provide or display instructions to the user via the fitness equipment. The instructions to the user may be through a display of the fitness equipment or may be audible instructions to the user. When the instructions are audible, the instructions may be transmitted to a head set of the user via a cable or wirelessly, e.g., via Bluetooth®.

The ECG device may detect contact with an electrode assembly of the ECG device (Step 314). If contact with the electrode assembly of the ECG device is not detected, the method 300 may include displaying or providing instructions to a user to grip or contact an electrode assembly of the ECG device (Step 316). Detecting contact with the electrode assembly may include detecting contact with a first electrode with a first or left hand of a user and detecting contact with a second electrode with a second or right hand of the user such that heart-related signals of the user may be detected with the electrode assembly. When contact is detected with the electrode assembly, the electrode assembly takes the initial ECG of the user as detailed above (Step 310). The method 300 may include providing instructions to a user continue to grip or contact the electrode assembly until the initial ECG is acquired (Step 318).

When the initial ECG of the user is taken, the initial ECG may be stored in memory of the ECG device or in memory of the computing device (Step 320). With the initial ECG stored, the method 300 may include providing instructions to a user to begin or resume activity such as exercise (e.g., walk or run on treadmill, pedal an exercise bike, resume riding, or resume running) (Step 330). In some embodiments, the method 300 may include initiating exercise including, but not limited to, starting a motor of the exercise equipment such that the movement of a user is required (e.g., starting to move a belt of a treadmill) (Step 332).

After a predetermined amount of time after the initial ECG is recorded, the method 300 includes taking or recording a subsequent or second ECG of the user (Step 340). The predetermined amount of time may be in a range of 5 minutes to 20 minutes (e.g., 10 minutes or 15 minutes). The second ECG may be taken when the user is stationary or at rest. The method 300 may include displaying or providing instructions to the user to be stationary (Step 342). As noted above, in some embodiments, the ECG device may be integrated into fitness equipment. In such embodiments, the ECG device may provide instructions to the user via the fitness equipment. The instructions to the user may be through a display of the fitness equipment or may be audible instructions to the user.

The ECG device may detect contact with the electrode assembly of the ECG device (Step 344). If contact with the electrode assembly of the ECG device is not detected, the method 300 may include providing or displaying instructions to a user to grip or contact an electrode assembly of the ECG device as described above (Step 346). When contact is detected with the electrode assembly, the electrode assembly takes the second ECG of the user as detailed herein (Step 340). The method 300 may include providing instructions to a user continue to grip or contact the electrode assembly until the second ECG is acquired (Step 348).

When the second ECG of the user is taken, the second ECG is stored in memory the ECG device or the computing device (Step 350). With the second ECG stored, the method 300 may include providing or displaying instructions to a user to resume exercise (Step 360). In some embodiments, the method 300 may include resuming exercise including, but not limited to, starting a motor of the exercise equipment such that the movement of a user is required (e.g., starting to move a belt of a treadmill) (Step 362).

With the first and second ECG, the computing device may analyze, compare, or process the first and second ECGs to evaluate conditions of the user (Step 370). The computing device may process the first and second ECGs to identify a health metric of the user including, but not limited to, heart rate or identify arrhythmias. The computing device may provide an indication of the health metric including if the health metric is normal or abnormal. The computing device or fitness equipment may display, store, and/or transmit the ECG or health metrics. The computing device or the fitness equipment may transmit the ECG, or health metrics in real-time to a web server by the computing device or the fitness equipment.

The method 300 may repeat taking or recording subsequent ECGs during exercise by repeating steps 340-370. When an exercise session is completed, the method may include taking or recording a final ECG of the user (Step 380). The exercise session may be terminated by the user or may be terminated after a predefined amount of session time. The session time may be in a range of 15 minutes to 2 hours (e.g., 30, 45, or 60 minutes). The final ECG may be taken when the user is stationary or at rest. The method 300 may include providing or displaying instructions to the user to be stationary (Step 382). As noted above, in some embodiments, the ECG device may be integrated into fitness equipment.

After the instructions for the user to be stationary, the ECG device may detect contact with the electrode assembly of the ECG device (Step 384). If contact with the electrode assembly of the ECG device is not detected, the method 300 may include providing instructions to a user to grip or contact an electrode assembly of the ECG device as described above (Step 386). When contact is detected with the electrode assembly, the electrode assembly takes the final ECG of the user as detailed herein (Step 380). The method 300 may include providing instructions to a user continue to grip or contact the electrode assembly until the final ECG is acquired (Step 388).

When the final ECG of the user is taken, the final ECG is stored in memory of the computing device (Step 390). With the final ECG stored, the computing device may analyze, compare, or process the first, second, any subsequent, and final ECGs to evaluate conditions of the user (Step 392). The computing device may process the first, second, and final ECGs to identify a health metric of the user including, but not limited to, heart rate or identify arrhythmias. The computing device may provide an indication of the health metric including if the health metric is normal or abnormal. The computing device or fitness equipment may display, store, and/or transmit the ECG or health metrics. The computing device or the fitness equipment may transmit the ECG, or health metrics in real-time to a web server by the computing device or the fitness equipment.

The method 300 may be used to capture heart related signals of a user. It may be advantageous to have a user stationary during the capture of heart related signals, as detailed above with respect to method 300, to reduce noise during the capture of heart related signals. For example, physiological signals to contract muscles or as a result of the contraction of muscles may create noise to heart related signals.

From the above descriptions, it is clear that the presently disclosed and claimed inventive concept(s) are well-adapted to carry out the objects and to attain the advantages mentioned herein, as well as those inherent in the presently disclosed and claimed inventive concept(s). While the presented embodiments have been described for purposes of this disclosure, it will be understood that numerous changes may be made which will readily suggest themselves to those skilled in the art and which are accomplished within the spirit of the presently disclosed and claimed inventive concept(s).

What is claimed is:

1. An apparatus comprising:
    sporting equipment;
    a sensor assembly including a first sensor and a second sensor, the first sensor integrated into the sporting equipment to contact skin of the user, the sensor assembly to produce electrical signals indicative of physiological signals of the user; and
    a processing device to generate an electrocardiogram (ECG) based on the electrical signals, wherein the ECG waveform represents a Lead I ECG.

2. The apparatus according to claim 1, wherein the sporting equipment comprises an exercise machine having a handle, the first sensor and the second sensor integrated into the handle of the exercise machine such that the first sensor and the second sensor are contacted by the user when the user interacts with the exercise machine.

3. The apparatus according to claim 2, wherein the first sensor is integrated into a first portion on the handle such that the first sensor is positioned to be contacted by a first hand of the user and the second sensor is integrated into a second portion on the handle such that the second sensor is positioned to be contacted by a second hand of the user that is different from the first hand.

4. The apparatus according to claim 2, wherein the sporting equipment comprises one of: a bicycle, an exercise bike, a treadmill, a stair machine, or an elliptical machine.

5. The apparatus according to claim 1, wherein the electrical signals are transmitted via Bluetooth® to a mobile device.

6. The apparatus according to claim 5, the processing device further to provide an ECG waveform of the ECG for display on the mobile device.

7. A system comprising:
    sporting equipment comprising:
        a body;
        a sensor assembly including a first sensor and a second sensor, the first sensor and the second sensor integrated into the body to contact skin of a user, wherein the sensor assembly produces electrical signals indicative of physiological signals of the user; and
        a processing device operatively coupled to the sensor assembly, the processing device to:
            generate electrocardiogram (ECG) data based on the electrical signals; and
            provide an ECG waveform of the ECG data for display on the mobile device,
            wherein the ECG waveform represents a Lead I ECG; and
    a mobile device communicatively coupled to the sporting equipment, the mobile device to display the ECG data.

8. The system according to claim 7, wherein the body comprises an exercise machine having a handle, the first sensor and the second sensor integrated into the handle such that the first sensor and the second sensor are positioned to be contacted by a user interacting with the exercise machine.

9. The system according to claim 8, wherein the first sensor is integrated into a first portion the handle such that the first sensor is positioned to be contacted by a first hand of a user, and wherein the second sensor is integrated into a second portion of the handle such that the second sensor is positioned to be contacted by a second hand of the user different from the first hand.

10. The system according to claim 8, wherein the exercise machine comprises one of: a bicycle, an exercise bike, a treadmill, a stair machine, or an elliptical machine.

11. The system according to claim 7, wherein the electrical signals are transmitted via Bluetooth® to the mobile device.

12. A method, comprising:
- recording a first electrocardiogram (ECG) of a user contacting an electrode assembly of an ECG device integrated into sporting equipment before an activity has begun;
- recording a second ECG of the user contacting the electrode assembly of the ECG device after the activity has finished;
- analyzing the first ECG and the second ECG; and
- providing an indication corresponding to a health metric of the user based on the analyzing.

13. The method according to claim 12, wherein recording the first ECG and recording the second ECG includes detecting contact with a handle of the sporting equipment, the handle being part of a bike, a stationary exercise bike, a treadmill, an elliptical machine, or a stair machine.

14. The method according to claim 13, further comprising providing instructions to the user to contact the handle before recording the first ECG and the second ECG.

15. The method according to claim 12, further comprising:
- recording a third ECG of the user contacting the electrode assembly of the ECG device during the activity, and
- analyzing the third ECG with the first ECG and the second ECG.

16. The method according to claim 12, wherein the indication indicates a normal or abnormal classification of the health metric of the user.

17. The apparatus of claim 1, wherein the sporting equipment comprises a helmet, and the first sensor is integrated into the helmet to contact a scalp of the user when the helmet is worn on a head of the user and the second sensor is integrated into an outside of the helmet to contact a limb of the user.

* * * * *